(12) United States Patent
Leonard et al.

(10) Patent No.: US 6,645,722 B2
(45) Date of Patent: *Nov. 11, 2003

(54) METHOD FOR SEQUENCING REACTION CLEANUP BY CONSTANT DIFFERENTIAL PRESSURE ULTRAFILTRATION

(75) Inventors: Jack T. Leonard, South Hamilton, MA (US); Constance MacDonald, Stoneham, MA (US); Joseph Gabriels, Arlington, MA (US)

(73) Assignee: Millipore Corporation, Bedford, MA (US)

(*) Notice: Subject to any disclaimer, the term of this patent is extended or adjusted under 35 U.S.C. 154(b) by 82 days.

This patent is subject to a terminal disclaimer.

(21) Appl. No.: 10/040,037

(22) Filed: Oct. 19, 2001

(65) Prior Publication Data

US 2002/0102593 A1 Aug. 1, 2002

Related U.S. Application Data

(63) Continuation of application No. 09/624,174, filed on Jul. 24, 2000.
(60) Provisional application No. 60/154,448, filed on Sep. 17, 1999.

(51) Int. Cl.[7] .................................................. C12Q 1/68
(52) U.S. Cl. ........................ 435/6; 435/91.1; 536/23.1; 210/650
(58) Field of Search ........................ 536/23.1; 435/91.1, 435/6; 210/650

(56) References Cited

U.S. PATENT DOCUMENTS

| | | | |
|---|---|---|---|
| 4,690,754 A | 9/1987 | Koyama et al. | 210/94 |
| 4,948,564 A | 8/1990 | Root et al. | 422/101 |
| 5,108,704 A | 4/1992 | Bowers et al. | 422/70 |
| 5,116,496 A | 5/1992 | Scott | 210/232 |
| 5,434,048 A | 7/1995 | Simon et al. | 435/6 |
| 5,665,247 A | 9/1997 | Valus et al. | 210/767 |
| 5,853,586 A | 12/1998 | Valus et al. | 210/406 |
| 5,856,100 A | 1/1999 | Hayashizaki | 435/6 |
| 5,876,936 A | 3/1999 | Ju | 435/6 |

FOREIGN PATENT DOCUMENTS

| | | |
|---|---|---|
| EP | 0 131 934 | 1/1985 |
| EP | 0 431 905 | 6/1991 |
| WO | 87/07645 | 12/1987 |
| WO | 92/13963 | 8/1992 |
| WO | 00/66723 | 11/2000 |

OTHER PUBLICATIONS

Applied and Theoretical Electrophoresis (1996) 6, 11–14; Joseph M. Devaney, et al.; "The evaluation of fast purification methods for preparing polymerase chain reaction (PCR) products for capillary electrophoresis analysis".

BioTechniques vol. 26, No. 5 (1999); Bjorn Magne Fangan, et al.; "Automated system for purification of dye–terminator sequencing products eliminates up–stream purification of templates"; pp. 980–983.

Journal of Chromatography B, 683 91996) 109–114; Phillip Belgrader, et al.; "Automated polymerase chain reaction product sample preparation for capillary electrophoresis analysis".

Rapid Communications in Mass Spectrometry. vol. 10, 1475–1478 (1996); Stephane Mouradian, et al.; "Analyzing sequencing reactions from bacteriophage M13 by matrix–assisted laser desorption/ionization mass spectrometry".

Anal. Chem. 1998, 70, 1516–1527; Marie C. Ruiz–Martinez, et al.; "A Sample purification method for rugged and high–performance DNA sequencing by capillary electrophoresis using replaceable polymer solutions. A. Development of the cleanup protocol".

Anal. Chem. 1998, 70, 1528–1535; Oscar Salas–Solano, et al.; "A Sample purification method for rugged and high–performance DNA sequencing by capillary electrophoresis using replaceable polymer solutions. B. Quantitative determination of the role of sample matrix components on sequencing analysis".

BioTechniques vol. 19, No. 2 (1995) pp. 176–177; Benchmarks; "Method for sequencing foreign genes expressed from the polyhedrin promoter of recombinant baculoviruses".

Membrane, 25 (4), 206–210 (2000); Ali Chaudry, et al.; "High throughput sample preparation using ultrafiltration in multiwell plate format: Post–sequencing cleanup of dye terminator sequencing reactions for capillary electrophoresis".

Anal. Chem. 1992, 64 2831–2835; "Capillary Ultrafiltration: In Vivo Sampling Probes for Small Molecules"; Michael C. Linhares et al.

*Primary Examiner*—James Ketter
(74) *Attorney, Agent, or Firm*—Nields & Lemack

(57) ABSTRACT

A method for sequencing reaction cleanup adapted to remove contaminants from a sequencing reaction, comprising the steps of: providing a defined quantity of sequencing reaction product; providing at least one ultrafiltration membrane having at least one surface; transferring the suspended sequencing reaction product to the surface of the ultrafiltration membrane; and applying a first constant pressure differential to the ultrafiltration membrane at a force capable of producing the sequencing reaction product substantially free of the contaminants.

11 Claims, 1 Drawing Sheet

METHOD FOR SEQUENCING REACTION CLEANUP BY CONSTANT DIFFERENTIAL PRESSURE ULTRAFILTRATION

This application is a continuation of Ser. No. 09/624,174 filed Jul. 24, 2000, which claims benefit of No. 60/154,448 filed Sep. 17, 1999.

FIELD OF THE INVENTION

This invention relates to a method of ultrafiltration. More specifically, the invention relates to a method for purifying sequencing reactions.

BACKGROUND OF THE INVENTION

Ultrafiltration with small devices is becoming a standard procedure used in DNA and protein research which is steadily requiring smaller and smaller quantities of materials. Methods of ultrafiltration have, in the past, relied on centrifugal forces to filter a liquid component through an ultrafiltration membrane. However, as the quantities of materials needed have become increasingly smaller, centrifugal methods no longer suit current needs, especially because these centrifugal methods are not conducive to automation.

Specifically, for example, DNA sequencing reactions must be purified prior to analysis by automated fluorescent sequencing (AFS) conducted on sequencing instruments such as the models ABI 377 and ABI 3700 from PE Biosystems, MegaBACE 1000 from Amersham Pharmacia Biotech and CEQ 2000 from Beckman. Introduction of the latter three high throughput capillary electrophoresis instruments has put new demands on sample purity and handling requirements.

Purification is required because contaminants that interfere with resolution of the sequencing products during electrophoretic separation will prevent determination of all or some of the DNA sequence. The identity of these interfering contaminants is determined, in part, by the sequencing chemistry used for labeling the sequencing products for fluorescent detection (e.g., dye primer or dye terminator chemistry), and the type of DNA sequencing instrument used for electrophoretic resolution of the labeled sequencing products (e.g., slab polyacrylamide gel or capillary electrophoresis).

Dye terminators are fluorescently labeled dideoxynucleotide triphosphates (ddNTP's) which, once incorporated in a base-specific manner, prevent further polymerization of the sequencing product. Primers, template, DNA polymerase, dNTP's, buffer, salts and dye terminators are added to a sequencing reaction at concentrations sufficient to allow production of sequencing products ranging from approximately 10 to 1200 nucleotides in length. Because dye terminators are not natural substrates of DNA polymerase, high concentrations must be provided relative to the natural dNTP substrates to ensure their incorporation into the polymerizing sequencing products. The consequence of this inefficient incorporation is that a large amount of unincorporated dye terminator is still present after the reaction is completed. Unincorporated dye terminators co-migrate with short sequencing products during electrophoresis, and produce a variety of artifacts that interfere with sequence analysis.

The most common methods for removing unincorporated dye terminators from sequencing reactions prior to electrophoresis are alcohol precipitation, typically using ethanol, and gel filtration. However, salts compete with sequencing products for electrokinetic injection onto capillary sequencing instruments and must also be removed. Ethanol precipitation has poor salt removal capabilities which detracts from its utility as a method for preparing samples prior to capillary electrophoresis because the efficiency of electrokinetic injection of sequencing products is inversely proportional to the salt concentration. As such, for purposes of removing these salts, alcohol precipitation is a poor and variable method for preparing samples. Although gel filtration is better suited for removing salt than alcohol precipitation, both gel filtration and alcohol precipitation are centrifuge-based methods which, as noted, are difficult to automate. Centrifugal methods are often sufficient for low throughput DNA sequencing carried out on older slab gel sequencing instruments, but the Genomics industry is scaling up DNA sequencing to a point where centrifugal sample preparation methods are no longer practical or sufficiently robust. Fueled by fierce competition and by new high throughput capillary DNA sequencing instruments, the Genomics industry is demanding unprecedented sample purity, automation capability and high throughput. However, such automatable methods, which are capable of removing salts and dye terminators, are not currently available.

Similarly, purified primer extension products may also be analyzed by gel analysis, such as capillary electrophoresis, or by mass spectrometry. For example, single nucleotide polymorphisms (SNPs) are single-base differences that genetically distinguish individuals within a population and as such can act as markers for diseases caused by the interaction of multiple genes. Differential termination of primer extension reactions is a commonly used method for detecting SNPs, whereby a dideoxy nucleotide analog is incorporated at the site of the sequence variation. Primer extension reactions contain many of the same components as sequencing reactions used to generate dideoxy-terminated sequencing ladders of indeterminant length. As such, the same contaminants must likewise be removed prior to analysis. The contaminants may comprise salts and dideoxy terminators, both of which pass through an ultrafiltration membrane, while the primer extension products do not.

SUMMARY OF THE INVENTION

It is therefore a primary object of this invention to provide a method for purifying DNA sequencing reactions or SNP assays that is capable of automation.

It is a further object of this invention to provide an automated method of ultrafiltration capable of removing salts and dye terminators.

It is a further object of this invention to provide a method of ultrafiltration capable of producing greater sample purity and recovery.

It is a further object of this invention to provide a method of ultrafiltration capable of high throughput.

It is a further object of this invention to provide an automated method for removing salts and dye terminators from DNA sequencing reactions capable of high throughput.

It is a further object of this invention to provide a method for removing salts from DNA sequencing reactions which is more efficient and consistent than salt removal by alcohol precipitation.

The method of the invention is the result of efforts to develop an ultrafiltration-based sequencing reaction cleanup method that is capable of automation and high throughput. Separation of impurities, such as salts and dye terminators, can be driven by vacuum using common laboratory equipment and, as such, is amenable to automation. Historically, ultrafiltration membranes in centrifugal devices were used to remove low molecular weight contaminants from higher molecular weight solutes, but fractionation can be time-consuming and inefficient. As noted, DNA sequencing reaction cleanup is a demanding separation wherein unincorporated fluorescent labels and salts must be removed from polymerase extension products in order to produce usable data. Unlike centrifugal ultrafiltration, which cannot produce sufficient purity, constant pressure differential ultrafiltration is used in the method of the invention to accomplish this critical separation. Constant pressure differential ultrafiltration provides highly pure results when the membrane and operating conditions are carefully controlled. An ultrafiltration membrane is employed to retain sequencing products while unincorporated fluorescent labels and salts pass through the membrane during constant pressure differential ultrafiltration.

As noted, constant pressure differential ultrafiltration offers excellent salt removal, fluorescent label removal and sequencing product recovery in a readily automated format. Vacuum-based or positive pressure-based manifolds used in the method are easier to automate than centrifugal ultrafiltration. Also, complete top access (no filtrate collection capabilities necessary) to the purified sequencing reaction allows direct electrokinetic injection from the surface of the ultrafiltration membrane, thereby simplifying sample processing and reducing the need for other consumables. Development of this novel protocol for processing sequencing reactions also eliminates artifacts which interfere with analyzing DNA sequence data.

A preferred method of the invention for sequencing reaction cleanup adapted to remove contaminants from a sequencing reaction, comprises the steps of: providing a defined quantity of sequencing reaction product; providing at least one ultrafiltration membrane having at least one surface; transferring the sequencing reaction product to the surface of the ultrafiltration membrane; and applying a first constant pressure differential to the ultrafiltration membrane at a force capable of producing the sequencing reaction product substantially free of the contaminants. For purposes of the method, the term "product" may comprise samples of varying purity from crude samples, to samples that are partially purified and may comprise liquids and/or solids. Also, the term "sequencing reaction" may comprise any polymerase extension reaction that produces a nucleic acid terminated in a dideoxynucleotide or modified dideoxynucleotide. For example, the term "sequencing reaction" may comprise primer extension reactions. The method of the invention may be employed at any point during the process for concentrating and purifying sequencing reaction product, e.g. at the beginning with a crude sample which includes template or towards the end of the purification process as a final purification step. The ultrafiltration membrane may have a molecular weight cutoff between about 1000 and 30,000 Daltons and preferably has a molecular weight cutoff between about 3,000 and 15,000 Daltons. When the contaminants to be removed comprise salt and/or dye terminators, the step of applying a first constant pressure differential to the ultrafiltration membrane preferably comprises applying a force capable of producing the sequencing reaction product substantially free of salts and/or dye terminators.

The method may further comprise the step of suspending the quantity of sequencing reaction product in a defined volume of a first solvent. The step of suspending the quantity of sequencing reaction product in a defined volume of a solvent may comprise adding one or more solvents including, but not limited to, 10–15% formamide, $\leq 0.5$ mM EDTA, and Milli-Q water to the sequencing reaction. Further, the step of applying a constant pressure differential to the ultrafiltration membrane may comprise applying vacuum at between about 5 to 28 inches of mercury, wherein the method may further comprise the steps of: washing the sequencing reaction product substantially free of the contaminants with a second solvent; and applying a second constant pressure differential to the ultrafiltration membrane, wherein the second constant pressure differential may also be applied at a force of between about 5 to 28 inches of mercury. The second solvent preferably comprises formamide, distilled water and/or EDTA.

The method may also further comprise the steps of: washing the sequencing reaction product substantially free of the contaminants with a third solvent; and applying a third constant pressure differential to the ultrafiltration membrane, wherein the third solvent may comprise Milli-Q water, formamide or EDTA. The third constant pressure differential vacuum is preferably applied at a force of between about 5 to 28 inches of mercury.

The method of the invention may further comprise the step of recovering the sequencing reaction product substantially free of the contaminants by pipetting off the surface of the membrane. In addition, the ultrafiltration membrane generally has an upstream and a downstream surface, wherein the suspended sequencing reaction product is transferred to and recovered from the upstream surface. The sequencing reaction product, substantially free of the contaminants, may be recovered from the retentate surface of the membrane by several methods including, but not limited to, pipetting, diffusion, agitation and electrokinetic transport. A vacuum force of about 5 inches of mercury may be applied during the recovery step to prevent any back migration of contaminants from the membrane substructure back to the retained material.

Depending on whether the product is to be analyzed by mass spectrometry or electrophoresis, the method may also comprise one or more of the following steps: washing said sequencing product with one or more salts capable of displacing any sodium ions from said product; resuspending said sequencing product, substantially free of one or more of said contaminants, in a matrix capable of crystallization; resuspending said sequencing product, substantially free of one or more of said contaminants, in water, EDTA or formamide for analysis by capillary electrophoresis; or resuspending said sequencing product, substantially free of one or more of said contaminants, in one or more volatile solvents for analysis by mass spectrometry.

As noted, the sequencing reaction product may comprise any polymerase extension reaction that produces a nucleic acid terminated in a dideoxynucleotide or modified dideoxynucleotide, including, but not limited to, one or more single nucleotide polymorphisms.

Another preferred method of the invention, for sequencing reaction cleanup adapted to remove contaminants from a sequencing reaction, comprises the steps of: providing a quantity of sequencing reaction product; suspending said quantity of sequencing reaction product in one or more solvents comprising formamide, EDTA and/or Milli-Q water; providing at least one ultrafiltration membrane having at least one surface; transferring said suspended sequencing reaction product to said surface of said ultrafiltration membrane; and applying a first constant pressure differential to said ultrafiltration membrane at a force between about 5 to 28 inches of mercury to produce said sequencing reaction product substantially free of said contaminants.

The method may further comprise the steps of: washing said sequencing reaction product substantially free of said contaminants with a second solvent; and applying a second constant pressure differential to said ultrafiltration membrane at a force between about 5 to 28 inches of mercury; wherein said second solvent preferably comprises formamide, EDTA and/or Milli-Q water. Still further, the method may comprise the steps of: washing said sequencing reaction product substantially free of said contaminants with a third solvent; and applying a third constant pressure differential to said ultrafiltration membrane; wherein said contaminants may comprise one or more salts and one or more dye terminators and wherein said step of applying a first constant pressure differential to said ultrafiltration membrane comprises applying a force capable of producing said sequencing reaction product substantially free of said salts and said dye terminators.

After the sequencing reaction product is substantially cleaned of the contaminents, the product may be resuspended in a matrix capable of crystallization, in water, formamide, EDTA or in one or more volatile solvents.

BRIEF DESCRIPTION OF THE DRAWING

Other objects, features and advantages will occur to those skilled in the art from the following description of the preferred method and the accompanying drawing in which.

DETAILED DESCRIPTION OF THE PREFERRED METHOD

Figure 1:
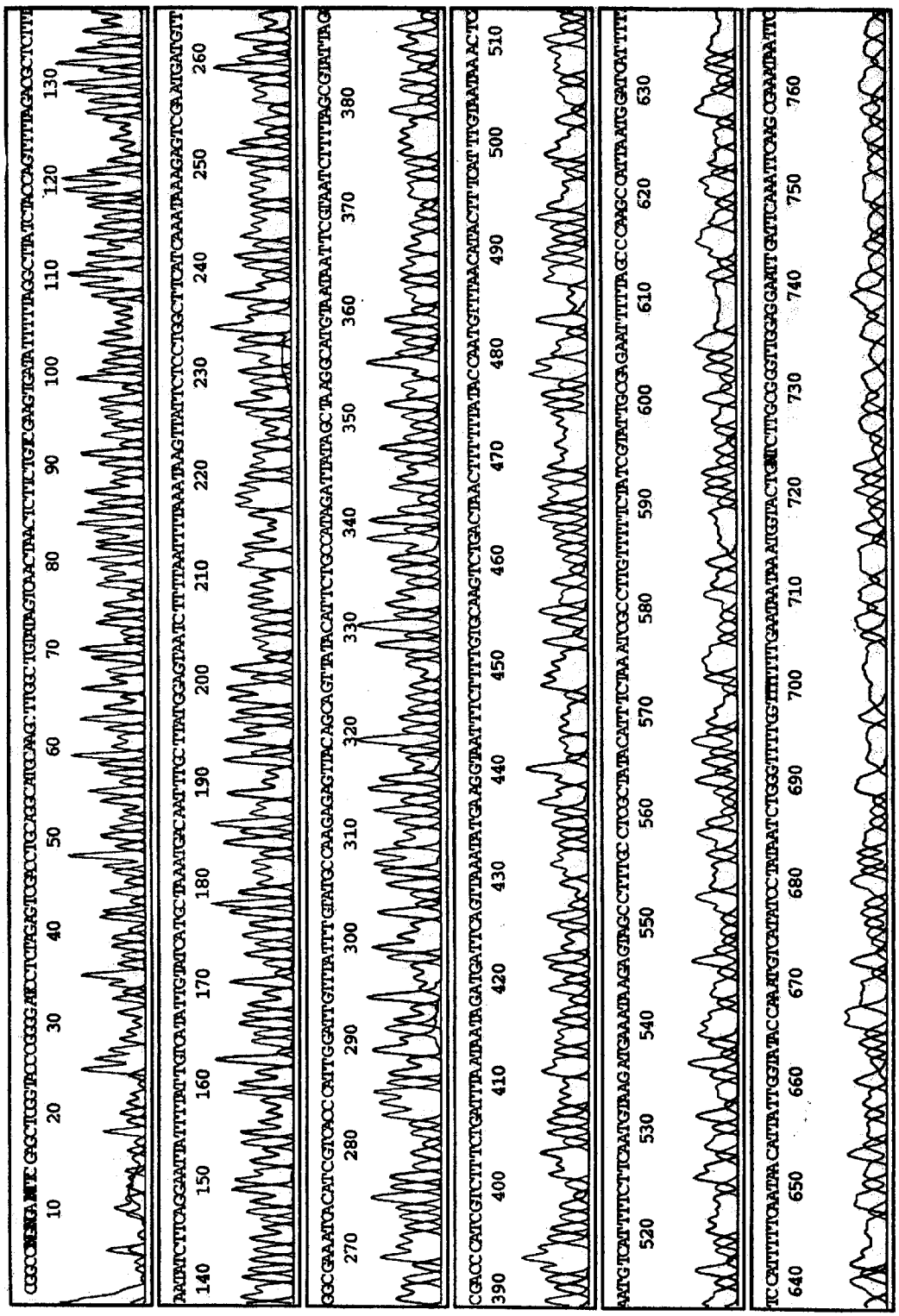
FIG. 1 is an electropherogram of a sequencing reaction sample purified by the method of the invention.

The method of the invention is adapted for sequencing reaction cleanup whereby contaminants such as salts and/or dye terminators are removed from a finished sequencing reaction to produce a purified DNA sequencing product capable of being analyzed using automated fluorescent sequencing devices such as the high throughput capillary electrophoresis instruments available from Perkin Elmer, Amersham Pharmacia Biotech and Beckman. FIG. 1 is an example of an electropherogram from such a capillary electrophoresis instrument of a sequencing reaction sample purified by the method of the invention herein disclosed using an ultrafiltration membrane having a molecular weight cutoff of about 10,000 Daltons.

The method of the invention uses a constant pressure differential as the driving force for the filtration process. High flow rates can be maintained for durations sufficient for most applications suited to using the method. The method enables one to separate low volumes of starting materials in a period of time that is substantially shorter than centrifugation. Additionally, constant pressure differential driven ultrafiltration is not subject to flux decay associated with centrifugal ultrafiltration which occurs over time with nonpolarizing solutes. As a consequence, constant pressure differential driven ultrafiltration enables one to achieve concentration factors that are much higher than the concentration factors of centrifugal ultrafiltration. Additionally, although flux decay is observable using constant pressure differential driven ultrafiltration with polarizing solutes such as concentrated proteins, constant pressure differential driven ultrafiltration is faster than centrifugal ultrafiltration in most situations. The process of constant pressure differential driven ultrafiltration reduces or eliminates the need for time-consuming repeat dilutions and filtrations that are frequently required with centrifugation to remove low molecular weight contaminants.

By "constant pressure differential" it is meant either a positive pressure or negative (or vacuum) pressure. Unlike the centrifugal method, in which the pressure is always decreasing over time due to a reduction in head height of the liquid, in a constant pressure differential method, the pressure acting on the liquid can remain constant over the filtration cycle. Additionally, since the pressure is independent of head height of the liquid on which it is acting it may even be increased over time in order to drive the filtration process to completion. It is also within this definition to have a decrease in pressure over time if desired. However unlike centrifugation, constant pressure differential allows such a decrease to be controlled, independent of head height of the liquid, which thus reduces or eliminates flux decay.

Ultrafiltration membranes are typically rated by their nominal molecular weight cutoff (i.e. the largest sized molecule which can pass through the particular membrane) rather than by average pore size (as with microfiltration membranes). In the present method, molecular cutoffs may range from about 100 Daltons (100 D) to about 500 kilo-Daltons (500 kD), depending on the point during the process of purification at which the method is employed. Ultrafiltration membranes can be made from a variety of materials including but not limited to polyamides, polysulphones, polyethersulphones polyarylsulphones, cellulosics, regenerated celluloses and polyvinylidene fluoride. They may be symmetrical or asymmetrical, although asymmetrical designs are preferred.

The method of the invention may be used to effectively purify biological material such as nucleic acids, proteins and other materials typically filtered using ultrafiltration. The method generally involves suspending a finished sequencing reaction in formamide, water and/or EDTA; tranferring the suspension to an ultrafiltration plate having a molecular weight cutoff between about 1000 to 30,000 Daltons; and subjecting the plate to a constant pressure differential at a vacuum, initially, of about 25 inches of mercury. For purposes of the invention, the term "sequencing reaction" comprises any polymerase extension reaction that produces a nucleic acid terminated in a dideoxynucleotide or modified dideoxynucleotide. Examples of such modified dideoxynucleotides include those that are modified with radioactive isotopes, fluorescent moieties, or mass tags, or any other modification that aids in the identification and/or detection of the terminating dideoxynucleotide. Specifically, for example, the term "sequencing reaction" includes both Sanger-type DNA sequencing reactions, which are used to generate dideoxy-terminated "sequencing ladders" of indeterminant length, and polymerase extensions which are deliberately dideoxy-terminated at a position one or several bases downstream of the genotyping primer. If the latter method is used to assay for single nucleotide polymorphisms (SNP's), one or more of the four deoxynucleotides (natural substrates of polymerase) are omitted from the sequencing reaction. This serves to make sequencing products of determinate length and predictable molecular weight, and to enable the multiplexing of genotyping primers without generating fragments that overlap in mass (MALDI-ToF mass spectrometry) or electrophoretic mobility (electrophoresis).

If using mass spectrometry to analyze the filtered product, an appropriate salt, such as ammonium citrate, may be used to wash or otherwise displace the sodium ions from the sequencing product prior to the mass spectrometry analysis. The sequencing product is preferably resuspended prior to mass spectrometry analysis using several alternative means, including, but not limited to, resuspending the product directly in a matrix suitable for crystllization; resuspending the product from the ultrafiltration membrane in water prior to spotting onto the MALDI target, allowing the spot to dry and overlaying the spot with a suitable matrix; or resuspending the product from the ultrafiltration membrane in a volatile solvent prior to spotting onto the MALDI target.

The method applies a constant pressure differential force to the retentate material for a relatively short period of time at a force sufficient to cause the contaminants to filter through the membrane at a substantially constant and efficient rate. The level of force applied depends on several factors including the amount of material to be filtered, the molecular weight cutoff of the membrane, the active filtration area of the membrane, the speed of filtration desired and the level of polarization of the material. It has been found that, for sequencing reaction product, the following membrane parameters and operating conditions achieve the best purity and are capable of being automated.

Once the sequencing reaction product is isolated, 10–15% formamide, $\leq 0.5$ mM EDTA and/or Milli-Q water is added to the finished sequencing reaction product inside a thermal cycling plate. Note, though, that the method of the invention is not necessarily limited to formamide, water or EDTA as the solvents. Other suitable solvents may be utilized having a similar positive effect and which are known in the art.

The suspended reaction material is then transferred to a 384 well ultrafiltration plate having a molecular weight cutoff (MWCO) of between about 1 kD to 30 kD. The ultrafiltration membrane preferably has a MWCO of between about 3 to 30 kD and more preferably between about 3 to 15 kD. The 384 ultrafiltration plate is then placed on a commonly available vacuum manifold. A vacuum is applied at between about 5 to 28 inches of mercury for between about 2 to 5 minutes or until the wells appear empty.

The retentate is then washed two times with a solvent comprising about 10–25 µl of 10–15% formamide, $\leq 0.5$ mM EDTA and/or Milli-Q water, available from Millipore, and a vacuum is applied a second time at between about 5 to 28 inches of mercury for the same amount of time using constant differential pressure. The retentate is washed again once with a solvent comprising about 10 µl of Milli-Q water or distilled water and a vacuum is applied at between about 5 to 28 inches of mercury. The purified sequencing product is then recovered by pipetting up and down 1 to 20 times on the surface of the membrane with about 10 µl of Mill-Q water, formamide or EDTA. A light vacuum of about 5 inches of mercury may be applied during the recovery step. The product may likewise be recovered using one or more diffusion, agitation and/or electrokinetic methods.

Modifications to the above described method may be made by those skilled in the art to optimize any particular variable to achieve the desired balance of speed, purity, recovery and automation. For example, one could conduct the entire separation using constant application of vacuum throughout the method. One could also consider sample pretreatment steps that would deplete higher molecular weight contaminants such as template DNA. In the latter case, one would utilize an ultrafiltration membrane having a molecular weight cutoff in the range of 100 kD to 500 kD, depending on the balance between sample properties (e.g. molecular weights), speed, template removal efficiency and sequencing product recovery requirements. Such modifications and others, in keeping with the purpose of the method of the invention, will occur to those skilled in the art and are within the following claims:

What is claimed is:

1. A method for sequencing reaction cleanup adapted to remove contaminants from a sequencing reaction, comprising the steps of, provide a quantity of sequencing reaction product;

providing at least one ultrafiltration membrane having at least one surface;

transferring said suspended sequencing reaction product to said surface of said ultrafiltration membrane;

applying a first constant pressure differential to said ultrafiltration membrane at a force capable of producing said sequencing reaction product substantially free of said contaminants; and recovering said sequencing reaction product substantially free of said contaminants by one or more steps selected from the group consisting of pipetting, diffusion, agitation and electrokinetic transport.

2. The method of claim 1, wherein said recovery is by electrokinetic transport.

3. The method of claim 2, wherein said ultrafiltration membrane has a molecular weight cutoff between about 3,000 and 15,000 Daltons.

4. The method of claim 2, further comprising suspending said quantity of sequencing reaction product in a first solvent.

5. The method of claim 4, wherein said step of suspending said quantity of sequencing reaction product in a solvent comprises adding one or more solvents selected from the group consisting of formamide, EDTA and water, to said sequencing reaction.

6. The method of claim 2, wherein said contaminants comprise salt and wherein said step of applying a first constant pressure differential to said ultrafiltration membrane comprises applying a force capable of producing said sequencing reaction product substantially free of salts.

7. A method for sequencing reaction cleanup adapted to remove contaminants from a sequencing reaction, comprising the steps of:

providing a quantity of sequencing reaction product comprising one or more single nucleotide polymorphisms;

providing at least one ultrafiltration membrane having at least one surface;

transferring said suspended sequencing reaction product to said surface of said ultrafiltration membrane;

applying a first constant pressure differential to said ultrafiltration membrane at a force capable of producing said sequencing reaction product substantially free of said contaminants.

8. The method of claim 7, further comprising recovering said sequencing reaction product substantially free of said contaminants by one or more steps selected from the group consisting of pipetting, diffusion, agitation and electrokinetic transport.

9. The method of claim 7, wherein said ultrafiltration membrane has a molecular weight cutoff between about 3,000 and 15,000 Daltons.

10. The method of claim 7, further comprising suspending said quantity of sequencing reaction product in a first solvent.

11. The method of claim 10, wherein said step of suspending said quantity of sequencing reaction product in a solvent comprises adding one or more solvents selected from the group consisting of formamide, EDTA and water, to said sequencing reaction.

* * * * *

SEQUENCE LISTING

<160> NUMBER OF SEQ ID NOS: 1

<210> SEQ ID NO 1
<211> LENGTH: 767
<212> TYPE: DNA
<213> ORGANISM: Escherichia coli bacteriophage lambda

<400> SEQUENCE: 1

```
cggccagtga attcgagctc ggtacccggg gatcctctag agtcgacctg caggcatgca      60
agcttggctg tatagtcaac taactcttct gtcgaagtga tattttttagg cttatctacc     120 agttttagac gctctttaat atcttcagga attattttat tgtcatattg tatcatgcta     180
aatgacaatt tgcttatgga gtaatctttt aatttttaaat aagttattct cctggcttca     240
tcaaataaag agtcgaatga tgttggcgaa atcacatcgt cacccattgg attgtttatt     300
tgtatgccaa gagagttaca gcagttatac attctgccat agattatagc taaggcatgt     360
aataattcgt aatcttttag cgtattagcg acccatcgtc tttctgattt aataatagat     420
gattcagtta aaatatgaagg taatttcttt tgtgcaagtc tgactaactt ttttatacca     480
atgtttaaca tactttcatt tgtaataaac tcaatgtcat tttcttcaat gtaagatgaa     540
ataagagtag cctttgcctc gctatacatt tctaaatcgc cttgttttc tatcgtattg     600 cgagaatttt tagcccaagc cattaatgga tcatttttcc attttttcaat aacattattg     660
```

```
ttataccaaa tgtcatatcc tataatctgg tttttgtttt tttgaataat aaatgttact      720
gttcttgcgg tttggaggaa ttgattcaaa ttcaagcgaa ataattc                    767
```